US012042591B2

(12) United States Patent
Furuhashi et al.

(10) Patent No.: US 12,042,591 B2
(45) Date of Patent: Jul. 23, 2024

(54) BLOOD PURIFICATION DEVICE

(71) Applicant: Nikkiso Company Limited, Tokyo (JP)

(72) Inventors: Tomohiro Furuhashi, Shizuoka (JP); Hideto Maki, Shizuoka (JP); Ferenc Kazinczi, Tokyo (JP); Yuji Yokota, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 411 days.

(21) Appl. No.: 17/598,507

(22) PCT Filed: Dec. 17, 2019

(86) PCT No.: PCT/JP2019/049465
§ 371 (c)(1),
(2) Date: Sep. 27, 2021

(87) PCT Pub. No.: WO2020/202657
PCT Pub. Date: Oct. 8, 2020

(65) Prior Publication Data
US 2022/0176029 A1    Jun. 9, 2022

(30) Foreign Application Priority Data

Apr. 1, 2019 (JP) .................................. 2019-069630

(51) Int. Cl.
*A61M 1/36* (2006.01)
*A61M 1/34* (2006.01)

(52) U.S. Cl.
CPC ........ *A61M 1/3624* (2013.01); *A61M 1/3468* (2014.02); *A61M 1/3486* (2014.02);
(Continued)

(58) Field of Classification Search
CPC .............. A61M 1/3437; A61M 1/3468; A61M 1/3486; A61M 1/3496; A61M 1/3624;
(Continued)

(56) References Cited

U.S. PATENT DOCUMENTS 8,758,603 B2    6/2014  Okazaki
2011/0284467 A1   11/2011  Okazaki
(Continued)

FOREIGN PATENT DOCUMENTS

CN    102215886 A    10/2011
CN    104721897 A     6/2015
(Continued)

OTHER PUBLICATIONS

International Search Report for Application No. PCT/JP2019/049465, dated Feb. 25, 2020.
(Continued)

*Primary Examiner* — John Kim
(74) *Attorney, Agent, or Firm* — Young Basile Hanlon & MacFarlane, P.C.

(57) ABSTRACT

A blood purification device includes a chamber, a liquid feed line, an air introduction unit, a liquid level adjustment unit, and a control unit. The chamber is provided on a blood circuit for extracorporeally circulating patient's blood and introduces purified plasma obtained by purifying plasma separated by a plasma separator provided on the blood circuit, or a replenishing liquid for replenishing the plasma separated by the plasma separator, into the blood circuit. The liquid feed line is capable of sending the purified plasma or the replenishing liquid to the chamber. The air introduction unit is capable of introducing air into the liquid feed line. The liquid level adjustment unit is capable of adjusting a liquid level height in the chamber. At the end of blood purification treatment, the control unit performs a liquid recovery process for sending the purified plasma or the replenishing liquid to the chamber via the liquid feed line while introducing air into the liquid feed line by the air introduction unit and maintains the liquid level height in the (Continued)

chamber at a predetermined liquid level height by the liquid level adjustment unit.

10 Claims, 5 Drawing Sheets

(52) U.S. Cl.
CPC ........ *A61M 1/3496* (2013.01); *A61M 1/3627* (2013.01); *A61M 1/3629* (2014.02); *A61M 1/3679* (2013.01); *A61M 1/3437* (2014.02); *A61M 2205/3382* (2013.01); *A61M 2205/3386* (2013.01)

(58) Field of Classification Search
CPC .............. A61M 1/3627; A61M 1/3629; A61M 1/3679; A61M 2205/3382; A61M 2205/3386
See application file for complete search history.

(56) References Cited

U.S. PATENT DOCUMENTS

| | | | |
|---|---|---|---|
| 2012/0083726 | A1 | 4/2012 | Kopperschmidt et al. |
| 2016/0310657 | A1 | 10/2016 | Solem et al. |
| 2017/0312412 | A1 | 11/2017 | Mochizuki |

FOREIGN PATENT DOCUMENTS

| | | | |
|---|---|---|---|
| EP | 0132047 | A1 | 1/1985 |
| JP | 61-193669 | A | 8/1986 |
| JP | S62142567 | A | 6/1987 |
| JP | H06-51057 | B2 | 7/1994 |
| JP | H06-51058 | B2 | 7/1994 |
| JP | 8-57043 | A | 3/1996 |
| JP | 4286165 | B2 | 6/2009 |
| JP | 2014184108 | A | 10/2014 |
| JP | 2017-35238 | A | 2/2017 |
| WO | 2010/058583 | A1 | 5/2010 |

OTHER PUBLICATIONS

European Search Report for Application No. 19922287.8, dated Oct. 28, 2022, 24 pgs.
Chinese Office Action for Application No. 201980094823.6 dated Dec. 6, 2023, with English translation, 17 pgs.

BLOOD PURIFICATION DEVICE

CROSS-REFERENCE TO RELATED APPLICATION(S)

This application is a continuation of International Application No. PCT/JP2019/049465, filed on Dec. 17, 2019, which claims priority to Japanese Application No. 2019-069630, filed on Apr. 1, 2019, the entire disclosures of which are hereby incorporated by reference.

TECHNICAL FIELD

The invention relates to a blood purification device.

BACKGROUND ART

In blood purification treatment called PA (Plasma Adsorption), DFPP (Double Filtration Plasmapheresis) or PE (Plasma Exchange), plasma is separated from blood of a patient, and then, purified plasma obtained by purifying the separated plasma or a replenishing liquid (a blood product such as fresh frozen plasma) is returned to the patient.

In blood purification devices for performing PA, DFPP or PE, plasma or a replenishing liquid remaining in a line through which plasma flows is generally recovered back to the patient while taking in air from a given position of the line after blood purification treatment (see, e.g., Patent Document 1).

CITATION LIST

Patent Literature

Patent Document 1: WO 2010/058583

SUMMARY OF INVENTION

Technical Problem

With the conventional blood purification devices, however, an alarm is generated in some cases because, e.g., excessive air is sent and air bubbles are detected by an air bubble detector located on a line for blood return to the patient. There are also cases where the plasma or replenishing liquid remains in the line due to insufficient air feed.

Therefore, it is an object of the invention to provide a blood purification device capable of recovering plasma or a replenishing liquid remaining in a line and also suppressing sending of air bubbles toward a patient after blood purification treatment.

Solution to Problem

To solve the problem mentioned above, the invention according to variation 1 provides a blood purification device comprising: a chamber that is provided on a blood circuit for extracorporeally circulating patient's blood and introduces purified plasma obtained by purifying plasma separated by a plasma separator provided on the blood circuit, or a replenishing liquid for replenishing the plasma separated by the plasma separator, into the blood circuit; a liquid feed line capable of sending the purified plasma or the replenishing liquid to the chamber; an air introduction unit capable of introducing air into the liquid feed line; a liquid level adjustment unit capable of adjusting a liquid level height in the chamber; and a control unit that, at an end of blood purification treatment, performs a liquid recovery process for sending the purified plasma or the replenishing liquid to the chamber via the liquid feed line while introducing air into the liquid feed line by the air introduction unit and maintaining the liquid level height in the chamber at a predetermined liquid level height by the liquid level adjustment unit.

The invention according to variation 2 is the blood purification device according to variation 1, wherein the liquid level adjustment unit is configured to be capable of increasing the liquid level height in the chamber by discharging air from the inside of the chamber.

The invention according to variation 3 is the blood purification device according to variation 2, comprising: a first liquid level detection sensor being provided at a first height position of the chamber and being capable of detecting whether or not a gas is present at the first height position in the chamber, wherein the control unit causes the liquid level adjustment unit to perform an operation of discharging air from the inside of the chamber when a gas is detected by the first liquid level detection sensor.

The invention according to variation 4 is the blood purification device according to variation 3, further comprising: a second liquid level detection sensor being provided at a second height position of the chamber, which is higher than the first height position, and being capable of detecting whether or not a gas is present at the second height position in the chamber, wherein the control unit starts discharge of air from the inside of the chamber by the liquid level adjustment unit when a gas is detected by the first and second liquid level detection sensors, and stops the discharge of air by the liquid level adjustment unit when a gas is not detected by the first and second liquid level detection sensors.

The invention according to variation 5 is the blood purification device according to variation 1, comprising: a liquid feed pump capable of sending the purified plasma or the replenishing liquid to the chamber, wherein, during the liquid recovery process, the control unit drives the liquid feed pump while introducing air into the liquid feed line by the air introduction unit and maintains the liquid level height in the chamber at a predetermined liquid level height by the liquid level adjustment unit.

The invention according to variation 6 is the blood purification device according to variation 5, wherein the liquid level adjustment unit comprises a level adjustment pump for discharging air from the inside of the chamber, and a discharge amount of the level adjustment pump is not less than a discharge amount of the liquid feed pump.

The invention according to variation 7 is the blood purification device according to variation 5, wherein the liquid level adjustment unit comprises a level adjustment pump for discharging air from the inside of the chamber, and the control unit ends the liquid recovery process by stopping the level adjustment pump and the liquid feed pump when an accumulated value of a rotation amount of the level adjustment pump becomes not less than a predetermined threshold.

The invention according to variation 8 is the blood purification device according to variation 5, wherein it is configured to discard the plasma separated by the plasma separator and introduce the replenishing liquid into the blood circuit, the liquid feed line comprises a replenishing liquid line for sending a replenishing liquid, and the liquid feed pump comprises a pump provided on the replenishing liquid line to send the replenishing liquid.

The invention according to variation 9 is the blood purification device according to variation 5, comprising: a plasma purifier for purifying plasma by adsorbing a specific component from the plasma separated by the plasma separator, wherein the liquid feed line comprises a purified plasma feed line for sending the purified plasma purified by the plasma purifier to the chamber, and the liquid feed pump comprises a waste liquid pump provided on a waste liquid line for sending the plasma separated by the plasma separator to the plasma purifier.

The invention according to variation 10 is the blood purification device according to variation 5, comprising: a plasma purifier for purifying plasma by separating a specific component from the plasma separated by the plasma separator, wherein the liquid feed line comprises a purified plasma feed line for sending a mixture of the purified plasma purified by the plasma purifier and the replenishing liquid to the chamber, and the liquid feed pump comprises a pump for sending the replenishing liquid to the plasma purifier.

The invention according to variation 11 is the blood purification device according to variation 5, wherein the liquid level adjustment unit comprises an atmosphere release valve allowing the interior of the chamber to be opened to atmosphere, and the control unit increases the liquid level height in the chamber by opening the atmosphere release valve and blocking the blood circuit on a downstream side of the chamber.

Advantageous Effects of Invention

According to the invention of variations 1 and 2, it is possible to provide a blood purification device capable of recovering plasma or a replenishing liquid remaining in a line and also suppressing sending of air bubbles toward a patient after blood purification treatment.

According to the invention of variations 2 and 3, it is possible to maintain the liquid level height in the chamber even if air is sent into the chamber.

According to the invention of variation 4, it is possible to maintain the liquid level height in the chamber in a given height range and to suppress frequent activation/stoppage of the liquid level adjustment unit.

According to the invention of variation 5, it is possible to easily send the purified plasma or the replenishing liquid to the chamber and to easily introduce air into the liquid feed line.

According to the invention of variation 6, it is possible to suppress sending of air bubbles toward the patient regardless of the delayed actuation of the level adjustment pump.

According to the invention of variation 7, it is possible to appropriately determine end time of the liquid recovery process.

According to the invention of variations 8, 9 and 10, a pump used in another application can be used as the liquid feed pump in case of performing PE, PA or DFPP, and the device can be reduced in size as compared to when separately providing a liquid feed pump.

According to the invention of variation 11, it is possible to omit the level adjustment pump and to reduce the size and cost of the device.

DESCRIPTION OF EMBODIMENTS

Embodiment

An embodiment of the invention will be described below in conjunction with the appended drawings.

Figure 1:
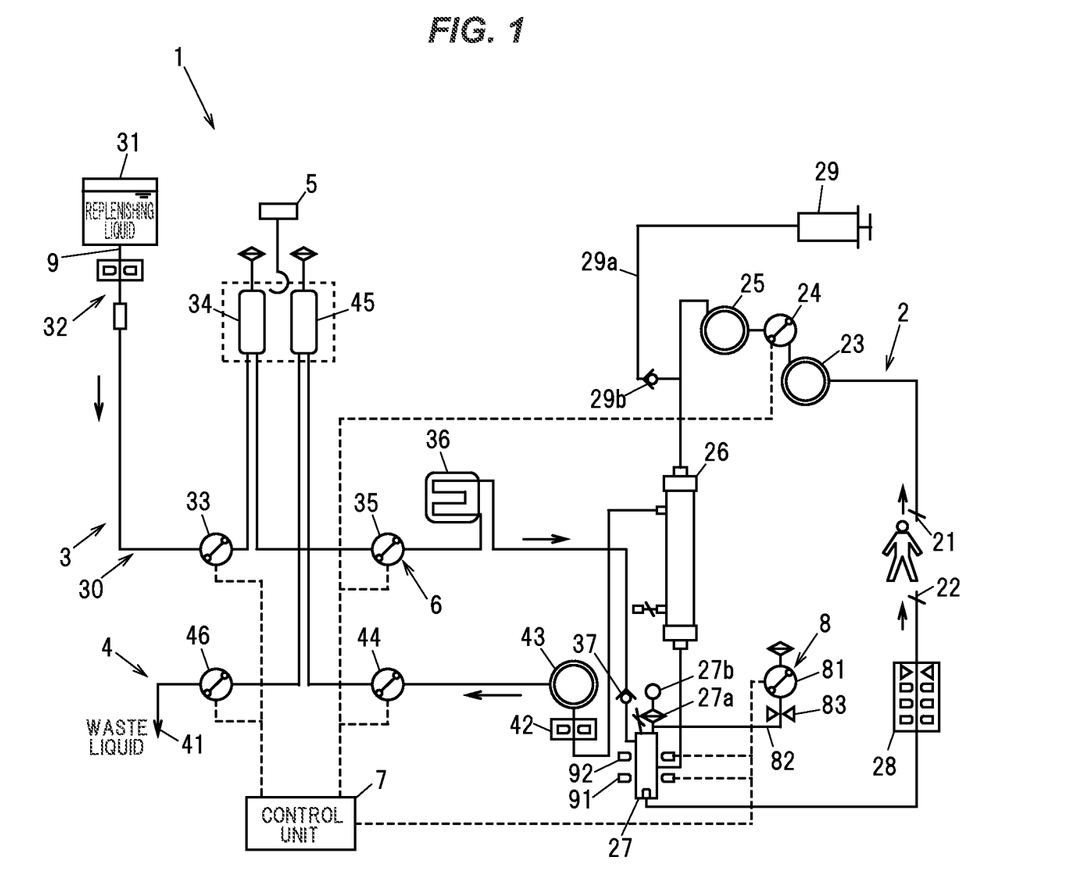
FIG. 1 is a schematic configuration diagram illustrating a blood purification device in an embodiment of the present invention.

FIG. 1 is a schematic configuration diagram illustrating a blood purification device in the present embodiment. A blood purification device 1 shown in FIG. 1 is a device for performing blood purification treatment called PE (Plasma Exchange) and is configured to discard plasma separated by a plasma separator 26 and introduce a replenishing liquid for replenishing the plasma separated by the plasma separator 26 (a blood product such as fresh frozen plasma or albumin preparation) into a blood circuit 2.

The blood purification device 1 includes a chamber 27 that is provided on the blood circuit 2 for extracorporeally circulating patient's blood and supplies a replenishing liquid (fresh plasma) to the blood circuit 2, a replenishing liquid line 30 as a liquid feed line 3 for sending the replenishing liquid, a total replacement pump 35 as a liquid feed pump 6 capable of sending the replenishing liquid, and a waste liquid line 4 for discharging the plasma separated by the plasma separator 26 provided on the blood circuit 2.

The blood circuit 2 is composed of, e.g., a flexible tube, etc. An artery-side puncture needle 21 is provided at one end of the blood circuit 2, and a vein-side puncture needle 22 is provided at the other end. In addition, a first pressure detector 23, a blood pump 24, a second pressure detector 25, the plasma separator 26, the chamber 27 and an air bubble detector 28 are sequentially provided on the blood circuit 2 from the artery-side puncture needle 21-side toward the vein-side puncture needle 22-side. The first pressure detector 23 is to detect pressure in the blood circuit 2 on the upstream side of the blood pump 24, and the second pressure detector 25 is to detect pressure in the blood circuit 2 on the downstream side of the blood pump 24. The air bubble detector 28 has an air bubble detection sensor for detecting air bubbles and a mechanism for clamping (gripping and blocking) the blood circuit 2 when air bubbles are detected.

The blood pump 24 is composed of a peristaltic pump that squeezes the tube to cause blood to flow toward the plasma separator 26. The plasma separator 26 is a device also called a dialyzer and separates plasma from blood by a membrane (not shown). The blood (blood cells, etc.) after separation of plasma by the plasma separator 26 is sent to the chamber 27. Meanwhile, the plasma separated by the plasma separator 26 is discharged into the waste liquid line 4. The chamber 27 serves to remove air bubbles and also serves to introduce (join) the replenishing liquid into the blood circuit 2. A pressure sensor 27b is connected to an upper part of the chamber 27 via a hydrophobic filter 27a.

An anticoagulant introduction line 29a for introducing an anticoagulant from a syringe pump 29 is connected to the blood circuit 2 between the second pressure detector 25 and the plasma separator 26. A check valve 29b is provided on the anticoagulant introduction line 29a so that blood flowing through the blood circuit 2 does not flow into the anticoagulant introduction line 29a.

The replenishing liquid line 30 is composed of, e.g., a flexible tube, etc. One end of the replenishing liquid line 30 is connected to a replenishing liquid bag 31 storing the replenishing liquid. The other end of the replenishing liquid line 30 is connected to the chamber 27. A replenishing liquid shortage detector 32, a replenishing liquid transfer pump 33, a replenishing liquid subdivision chamber 34, the total replacement pump 35, a warmer 36 and a check valve 37 are sequentially provided on the replenishing liquid circuit 30 from the replenishing liquid bag 31-side toward the chamber 27-side.

The replenishing liquid shortage detector 32 is to detect shortage of the replenishing liquid. The replenishing liquid transfer pump 33 is a pump for transferring the replenishing liquid stored in the replenishing liquid bag 31 to the replenishing liquid subdivision chamber 34. The replenishing liquid subdivision chamber 34 is a chamber for temporarily storing the replenishing liquid. The total replacement pump 35 is a pump for sending the replenishing liquid stored in the replenishing liquid subdivision chamber 34 toward the chamber 27. The warmer 36 warms the replenishing liquid. The check valve 37 is a valve for suppressing the backflow of the liquid from the blood circuit 2-side toward the replenishing liquid line 30. The replenishing liquid transfer pump 33 and the total replacement pump 35 are each composed of a peristaltic pump that squeezes the tube to cause the replenishing liquid to flow.

The waste liquid line 4 is composed of, e.g., a flexible tube, etc. One end of the waste liquid line 4 is connected to the plasma separator 26 and the other end serves as a discharge port 41 for discharging a waste liquid. A blood leakage detector 42, a third pressure detector 43, a waste liquid pump 44, a waste liquid subdivision chamber 45 and a waste liquid transfer pump 46 are sequentially provided on the waste liquid line 4 from the plasma separator 26-side toward the discharge port 41.

The blood leakage detector 42 is a detector for detecting whether a component other than plasma, such as blood cells, is leaking toward the waste liquid line 4 due to damage, etc., on the plasma separator 26. The third pressure detector 43 is a detector for detecting pressure in the waste liquid line 4 on an inlet side of the waste liquid pump 44. The waste liquid pump 44 sends the plasma separated by the plasma separator 26 (the waste liquid) to the waste liquid subdivision chamber 45. The waste liquid subdivision chamber 45 is to temporarily store the plasma (the waste liquid). The waste liquid transfer pump 46 is a pump for transferring the plasma (the waste liquid) stored in the waste liquid subdivision chamber 45 to the discharge port 41. The waste liquid pump 44 and the waste liquid transfer pump 46 are each composed of a peristaltic pump that squeezes the tube to cause the plasma (the waste liquid) to flow.

The blood purification device 1 also includes a load meter 5 for detecting a total weight of the replenishing liquid subdivision chamber 34 and the waste liquid subdivision chamber 45. The blood purification device 1 repeats a first step in which the replenishing liquid stored in the replenishing liquid bag 31 is transferred to the replenishing liquid subdivision chamber 34 by the replenishing liquid transfer pump 33 and the plasma (the waste liquid) stored in the waste liquid subdivision chamber 45 is discharged by the waste liquid transfer pump 46, and a second step in which the replenishing liquid stored in the replenishing liquid subdivision chamber 34 is supplied toward the chamber 27 and the plasma (the waste liquid) from the plasma separator 26 is accumulated in the waste liquid subdivision chamber 45. In the second step, the weight detected by the load meter 5 is constant when a supply amount of the replenishing liquid and a discharge amount of the plasma (the waste liquid) are equal. Therefore, in the blood purification device 1, rotational speeds (discharge amounts) of the total replacement pump 35 and the waste liquid pump 44 are controlled so that the weight detected by the load meter 5 in the second step is constant.

Each of the pumps 24, 33, 35, 44, 46 is controlled by a control unit 7. The control unit 7 is realized by appropriately combining an arithmetic element such as CPU, a memory, a storage device, a software, and an interface, etc.

The blood purification device 1 further includes an air introduction unit 9 that can introduce air into the replenishing liquid line 30 during the liquid recovery process. In the present embodiment, the air introduction unit 9 is configured to be able to introduce air into the replenishing liquid line 30 by pulling one end of the replenishing liquid line 30 out of the replenishing liquid bag 31 (see FIG. 2). However, the specific configuration of the air introduction unit 9 is not limited thereto, and the configuration may be such that, e.g., air is introduced from the replenishing liquid subdivision chamber 34. Alternatively, the air introduction unit 9 may be configured to push air into the replenishing liquid line 30 by, e.g., an air pump, etc.

The blood purification device 1 in the present embodiment includes a liquid level adjustment unit 8 capable of adjusting a liquid level height in the chamber 27. At the end of the blood purification treatment, the control unit 7 performs a liquid recovery process for sending the replenishing liquid to the chamber 27 via the liquid feed line 3 by driving the liquid feed pump 6 (the total replacement pump 35 here) while supplying air into the replenishing liquid line 30 by the air introduction unit 9 and maintaining the liquid level height in the chamber 27 at a predetermined liquid level height by the liquid level adjustment unit 8.

Figure 2:
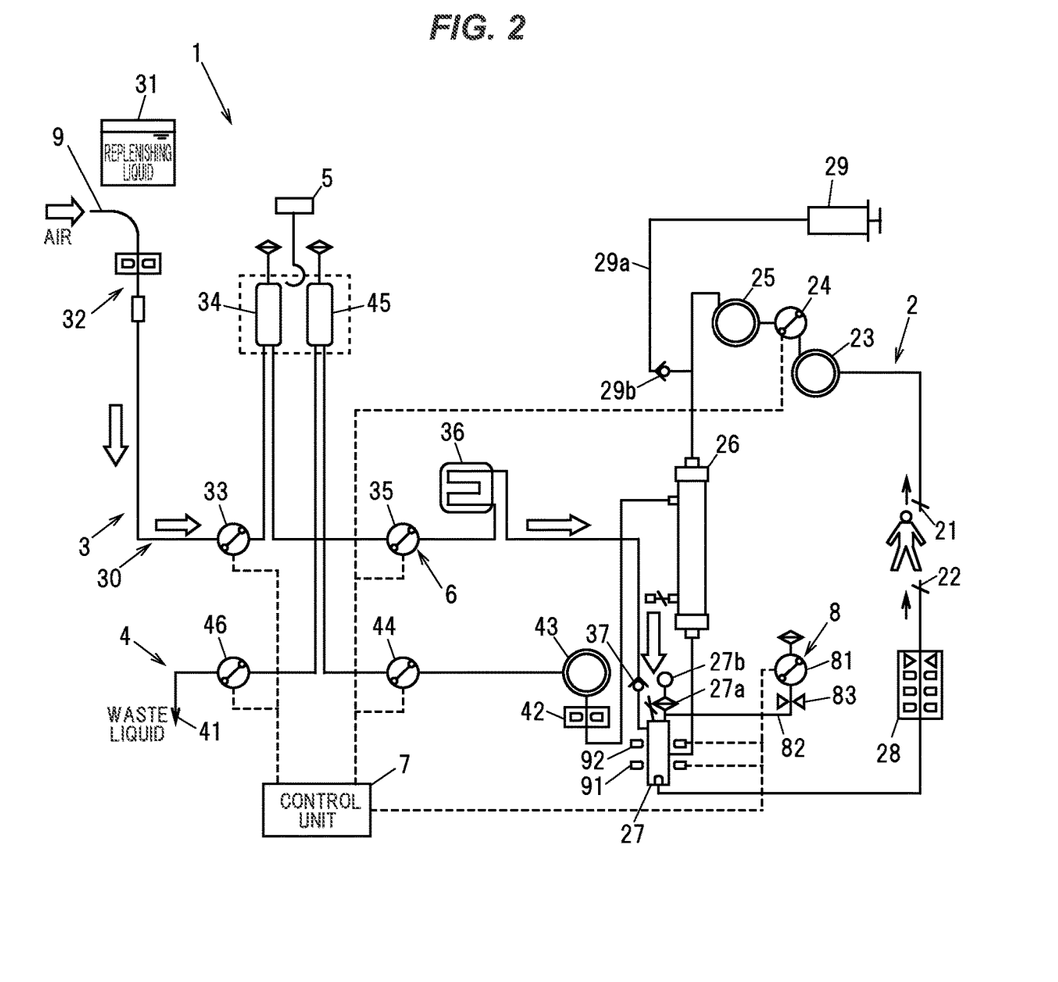
FIG. 2 is an explanatory diagram illustrating flows of air and a replenishing liquid in the blood purification device of FIG. 1 during a liquid recovery process.

FIG. 2 is an explanatory diagram illustrating flows of air and the replenishing liquid in the blood purification device 1 during the liquid recovery process. As shown in FIG. 2, in the present embodiment, the total replacement pump 35 as the liquid feed pump 6 is driven during the liquid recovery process while introducing air into the replenishing liquid line 30. Thus, the replenishing liquid in the replenishing liquid line 30 is replaced with air, and the replenishing liquid remaining in the replenishing liquid line 30 is sent to the chamber 27. In the present embodiment, both the total replacement pump 35 and the replenishing liquid transfer pump 33 are driven since the air is not sent toward the chamber 27 if the replenishing liquid transfer pump 33 remains stopped.

At this time, if excessive air is sent, the liquid level in the chamber 27 is lowered and air bubbles may flow toward the air bubble detector 28. Therefore, in the present embodiment, the liquid level height in the chamber 27 is maintained at a predetermined liquid level height by the liquid level adjustment unit 8 during the liquid recovery process to suppress flow of air bubbles to the downstream side of the chamber 27 (the air bubble detector 28 side).

The liquid level adjustment unit 8 is configured to be capable of increasing the light level height in the chamber 27 by discharging air from the inside of the chamber 27. In the present embodiment, the liquid level adjustment unit 8 has a level adjustment pump 81 for discharging air from the inside of the chamber 27. The level adjustment pump 81 is connected to the chamber 27 via an air discharge line 82. A clamp 83 capable of blocking the air discharge line 82 is provided on the air discharge line 82.

The blood purification device 1 also includes a first liquid level detection sensor 91 that is provided at a first height position of the chamber 27 and is capable of detecting whether or not a gas is present at the first height position in the chamber 27. The control unit 7 controls the liquid level adjustment unit 8 so that the liquid level height does not become lower than the first height. In particular, when a gas is detected by the first liquid level detection sensor 91, the control unit 7 drives the level adjustment pump 81 to cause it to perform an operation of discharging air from the inside of the chamber 27.

In the present embodiment, a second liquid level detection sensor 92 is further included, which is provided at a second height position of the chamber 27, which is higher than the first height position, and is capable of detecting whether or not a gas is present at the second height position in the chamber 27. The control unit 7 controls the liquid level adjustment unit 8 so that the liquid level height is between the first height and the second height. In particular, the control unit 7 starts discharge of air from the inside of the chamber 27 by driving the level adjustment pump 81 when a gas is detected by the first and second liquid level detection sensors 91, 92, and stops the discharge of air by stopping the level adjustment pump 81 when a gas is not detected by the first and second liquid level detection sensors 91, 92. Thus, it is possible to suppress frequent activation/stoppage of the level adjustment pump 81 and thereby suppress a load on the level adjustment pump 81.

Optionally, a liquid level detection sensor for continuously measuring the liquid level height in the chamber 27 may be provided. In this case, based on the detection result from the liquid level detection sensor, the blood purification device 1 determines whether or not the liquid level height in the chamber 27 is higher than the first height position and whether or not the liquid level height in the chamber 27 is lower than the second height.

The level adjustment pump 81 is composed of a peristaltic pump that squeezes the tube to cause the air to flow. The replenishing liquid transfer pump 33 and the total replacement pump 35 continue to be driven during the liquid recovery process, but the level adjustment pump 81 is actuated at the middle of the process and thus cannot avoid a slight delay in air discharge. To cover this delay, the discharge amount (the pump speed) of the level adjustment pump 81 is desirably not less than the discharge amount (the pump speed) of the liquid feed pump 6 (the total replacement pump 35), and further desirably, the discharge amount (the pump speed) of the level adjustment pump 81 is more than the discharge amount (the pump speed) of the liquid feed pump 6 (the total replacement pump 35). In addition, the liquid level may be adjusted by driving the level adjustment pump 81 in a state in which the liquid feed pump 6 is stopped (the discharge amount (the pump speed) of zero). Furthermore, the liquid feed pump 6 may be repeatedly driven and stopped intermittently. In this case, the discharge amount (the pump speed) of the level adjustment pump 81 should be more than an average value of the discharge amount of the liquid feed pump 6.

After a predetermined time by which the operation of the level adjustment pump 81 is considered to be stabilized has elapsed, the discharge amount (the pump speed) of the level adjustment pump 81 may be controlled to be equal to the discharge amount (the pump speed) of the liquid feed pump 6 (the total replacement pump 35). In other words, the discharge amount (the pump speed) of the level adjustment pump 81 may be controlled to be greater than the discharge amount (the pump speed) of the liquid feed pump 6 (the total replacement pump 35) for a predetermined time from the start of driving, and controlled to be equal to the discharge amount (the pump speed) of the liquid feed pump 6 (the total replacement pump 35) after the predetermined time has elapsed. Although the example in which the discharge amount of the level adjustment pump 81 is changed has been described here, the discharge amount (the pump speed) of the level adjustment pump 81 may be controlled to be not less than the discharge amount (the pump speed) of the liquid feed pump 6 (the total replacement pump 35) by changing (decreasing) the discharge amount of the liquid feed pump 6 (the total replacement pump 35).

The level adjustment pump 81 is also provided with a rotation amount detection unit capable of detecting the rotation amount thereof. As the rotation amount detection unit, it is possible to use, e.g., an encoder, etc. When a stepping motor is used for driving the level adjustment pump 81, it is possible to know the rotation amount also based on the number of pulses output to the stepping motor.

The control unit 7 calculates an accumulated value of the rotation amount of the level adjustment pump 81 based on the detection result from the rotation amount detection unit, and ends the liquid recovery process by stopping the level adjustment pump 81 and the liquid feed pump 6 when the accumulated value of the rotation amount becomes not less than a predetermined threshold. At this time, both the total replacement pump 35 and the replenishing liquid transfer pump 33 are stopped. Meanwhile, the blood pump 24 continues to be driven to suppress blood coagulation. When the number of revolutions of the level adjustment pump 81 can be regarded constant, the liquid recovery process may be ended by stopping the level adjustment pump 81 and the liquid feed pump 6 when operating time of the level adjustment pump 81 becomes not less than a predetermined threshold.

Figure 3:
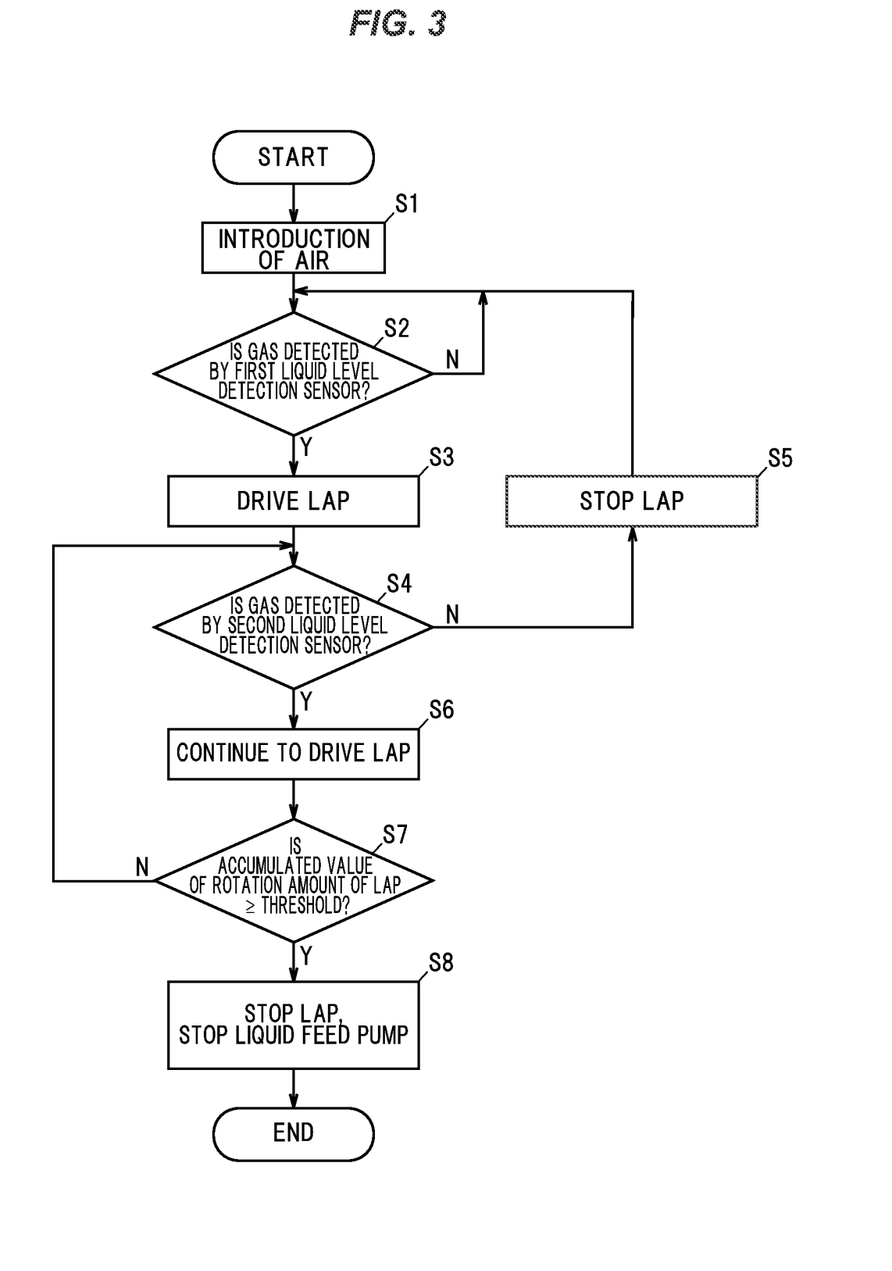
FIG. 3 is a flowchart showing a control flow of the liquid recovery process.

Now, a control flow of the liquid recovery process will be described. FIG. 3 is a flowchart showing the control flow of the liquid recovery process. The liquid recovery process is performed at the end of the blood purification treatment.

In the liquid recovery process, firstly, air is introduced into the liquid feed line 3 (the replenishing liquid line 30) by the air introduction unit 9 in Step S1, as shown in FIG. 3. In the present embodiment, air is introduced into the replenishing liquid line 30 by pulling one end of the replenishing liquid line 30 out of the replenishing liquid bag 31. At this time, both the total replacement pump 35 and the replenishing liquid transfer pump 33 are in the operating state.

After that, in Step S2, the control unit 7 determines whether a gas is detected by the first liquid level detection sensor 91. When the determination made in Step S2 is NO, the process returns to Step S2. When the determination made in Step S2 is YES, the level adjustment pump (LAP) 81 is driven in Step S3 to start discharge of air from the inside of the chamber 27.

After that, in Step S4, the control unit 7 determines whether a gas is detected by the second liquid level detection sensor 92. When the determination made in Step S4 is NO, the level adjustment pump 81 is stopped in Step S5 and the process then returns to Step S2. When the determination made in Step S4 is YES, the level adjustment pump 81 continues to be driven in Step S6 and it is then determined in Step S7 whether the accumulated value of the rotation amount of the level adjustment pump 81 has become not less than the predetermined threshold. When the determination made in Step S7 is NO, the process returns to Step S4.

When the determination made in Step S7 is YES, the level adjustment pump 81 and the liquid feed pump 6 are stopped in Step S8. In the present embodiment, both the total replacement pump 35 and the replenishing liquid transfer pump 33 are stopped. After that, the process ends.

Modification

Although the liquid level adjustment unit 8 is composed of the level adjustment pump 81 in the present embodiment, the specific configuration of the liquid level adjustment unit 8 is not limited thereto. The liquid level adjustment unit 8 may be, e.g., an atmosphere release valve allowing the interior of the chamber 27 to be opened to atmosphere. In this case, the control unit 7 increases the liquid level height in the chamber 27 by sending plasma using the liquid feed pump 6 while opening the atmosphere release valve and blocking the blood circuit 2 on the downstream side of the chamber 27. Blocking of the blood circuit 2 on the downstream side of the chamber 27 may be achieved by, e.g., using a clamp of the air bubble detector 28 or providing a dedicated clamping device or an on/off valve, etc. Since such a configuration allows the level adjustment pump 81 to be omitted, it is possible to simplify the device and reduce the size and cost of the device.

When the atmosphere release valve is used as the liquid level adjustment unit 8 and the blood circuit 2 is blocked by using the clamp of the air bubble detector 28, the atmosphere release valve is opened in response to detection by the first liquid level detection sensor 91 and, after the clamp of the air bubble detector 28 is operated (after the blood circuit 2 is blocked), the liquid feed pump 6 is stopped being driven on condition that the accumulated value of the rotation amount of the liquid feed pump 6 has reached a specified value.

Functions and Effects of the Embodiment

As described above, the blood purification device 1 in the present embodiment is configured that, during the liquid recovery processing, the replenishing liquid is sent to the chamber 27 via the liquid feed line 3 while introducing air into the liquid feed line 3 by the air introduction unit 9 and the liquid level height in the chamber 27 is maintained at a predetermined liquid level height by the liquid level adjustment unit 8.

With such a configuration, it is possible to recover the replenishing liquid remaining in the liquid feed line 3 and also to suppress sending of air bubbles toward the patient after blood purification treatment. As a result, generation of an alarm due to detection of air bubbles by the air bubble detector 28 is suppressed during the liquid recovery process and it is thus possible to reduce burden on workers.

Other Embodiments

Figure 4:
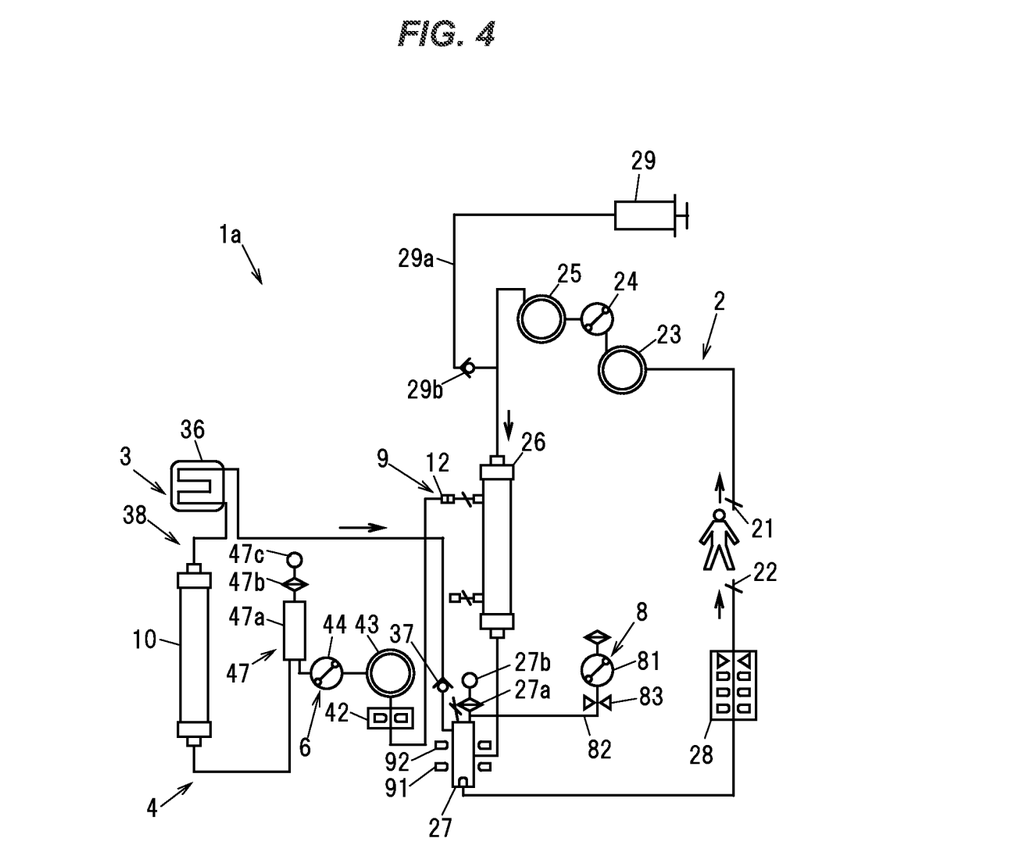
FIG. 4 is a schematic configuration diagram illustrating the blood purification device in another embodiment of the invention.

A blood purification device 1a shown in FIG. 4 is a device for performing blood purification treatment called PA (Plasma Adsorption). The same members as those of the blood purification device 1 shown in FIG. 1 are denoted by the same reference numerals in FIG. 4 and the description of these members will omitted.

In the blood purification device 1a, a detachable connector 12 is provided at the most upstream of the waste liquid line 4 (in the vicinity of the plasma separator 26) and the air introduction unit 9 is configured to be able to introduce air into the waste liquid line 4 by detaching the connector 12. The air introduction unit 9, however, is not limited thereto and may be configured to introduce air by, e.g., opening a port of the plasma separator 26 on the opposite side to a plasma output side or may be configured to introduce air into a chamber 47a of a secondary membrane pressure port 47 (described later).

In addition, the waste liquid line 4 of the blood purification device 1a is configured that the plasma separated by the plasma separator 26 is sent to a plasma purifier (a selective-type plasma component adsorber) 10. An end of the waste liquid line 4 on the opposite side to the plasma separator 26 is connected to the plasma purifier 10. The plasma purifier 10 is also called a selective-type plasma component adsorber which adsorbs a specific component from the plasma separated by the plasma separator 26 and thereby purifies the plasma.

The secondary membrane pressure port 47 is provided on the waste liquid line 4 between the plasma purifier 10 and the waste liquid pump 44. The secondary membrane pressure port 47 has the chamber 47a and a pressure sensor 47c provided on the chamber 47a via a hydrophobic filter 47b. The secondary membrane pressure port 47 serves to separate air bubbles from plasma to be introduced into the plasma purifier 10 and also serves to measure pressure on an inlet side of the plasma purifier 10.

The purified plasma purified by the plasma purifier 10 is sent to the chamber 27 through a purified plasma feed line 38. The warmer 36 for warming the purified plasma and the check valve 37 are provided on the purified plasma feed line 38.

In the blood purification device 1a, the waste liquid pump 44 is used as the liquid feed pump 6 for sending the purified plasma and air during the liquid recovery process. In more particular, the blood purification device 1a is configured that, during the liquid recovery process, the connector 12 is detached to allow air to be introduced and the waste liquid pump 44 is driven. Thus, the plasma in the waste liquid line 4, the plasma purifier 10 and the purified plasma feed line 38 is replaced with air and the purified plasma is recovered back to the patient.

In addition, in the blood purification device 1a, the liquid level height in the chamber is maintained at a predetermined liquid level height by the liquid level adjustment unit 8 during the liquid recovery process in the same manner as the blood purification device 1 described above. In particular, the control unit 7 starts discharge of air from the inside of the chamber 27 by driving the level adjustment pump 81 when a gas is detected by the first and second liquid level detection sensors 91, 92, and stops the discharge of air by stopping the level adjustment pump 81 when a gas is not detected by the first and second liquid level detection sensors 91, 92. The control unit 7 also calculates the accumulated value of the rotation amount of the level adjustment pump 81 and ends the liquid recovery process by stopping the level adjustment pump 81 and the liquid feed pump 6 (the waste liquid pump 44 here) when the accumulated value of the rotation amount becomes not less than the predetermined threshold.

Figure 5:
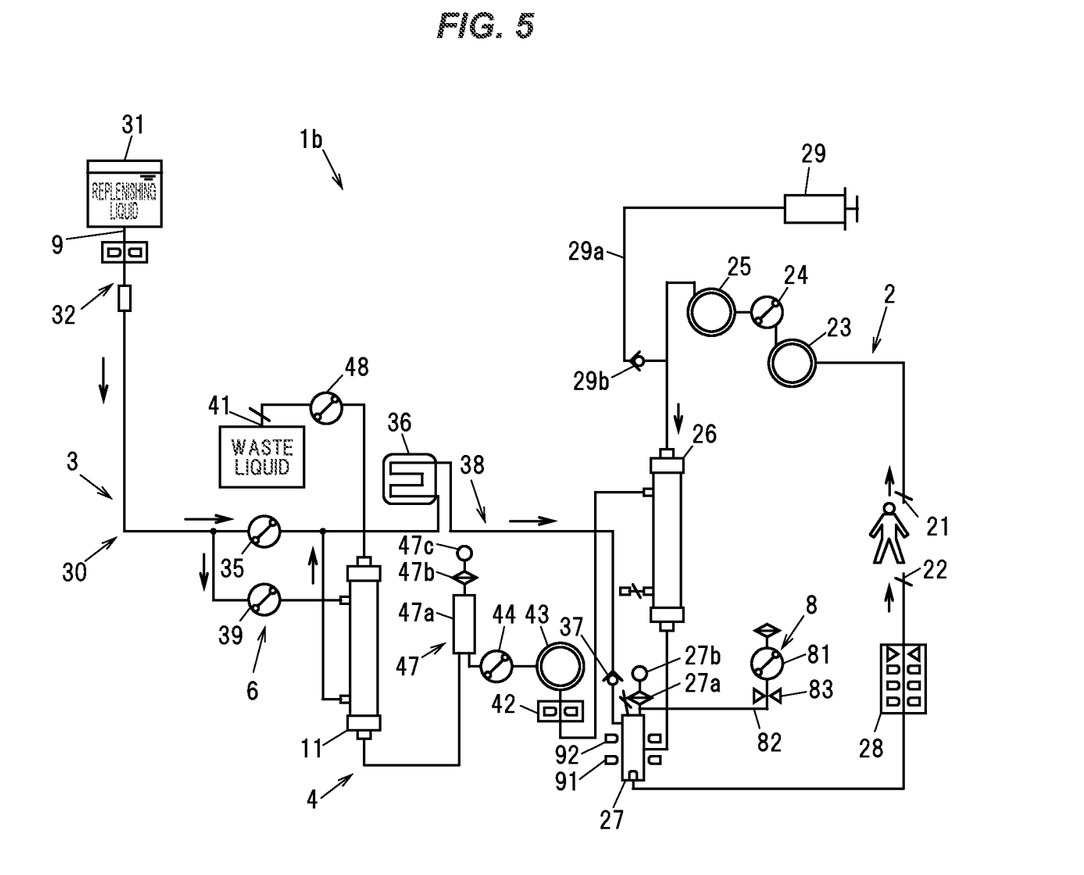
FIG. 5 is a schematic configuration diagram illustrating the blood purification device in another embodiment of the invention.

A blood purification device 1b shown in FIG. 5 is a device for performing blood purification treatment called DFPP (Double Filtration Plasmapheresis).

The blood purification device 1b includes a plasma purifier 11 for purifying plasma by further separating a specific component from the plasma separated by the plasma separator 26. The plasma purifier 11 is also called a plasma component separator and is configured so that only a specific component (a normal component) of plasma is extracted and added to the replenishing liquid by bringing the replenishing liquid into contact with the plasma through a membrane.

The blood purification device 1b is similar to the blood purification device 1a of FIG. 4 but is configured that the plasma purifier 11 and a second waste liquid pump 48 are sequentially provided on the waste liquid line 4 on the downstream side of the secondary membrane pressure port 47 and the other end of the waste liquid line 4 serves as the discharge port 41 for discharging the waste liquid (the plasma). In addition, the purified plasma feed line 38 is provided so as to connect a replenishing liquid outlet of the plasma purifier 11 to the chamber 27. Furthermore, the replenishing liquid line 30 extending from the replenishing liquid bag 31 is branched into two, one of branches is connected to a replenishing liquid inlet of the plasma purifier 11 via a pre-replacement pump 39 and the other branch is connected via the total replacement pump 35 to the purified plasma feed line 38 on the downstream side of the plasma purifier 11. In the blood purification device 1b, the purified plasma and the replenishing liquid are mixed and sent to the chamber 27 through the purified plasma feed line 38.

The air introduction unit 9 of the blood purification device 1b is also configured to be able to introduce air into the replenishing liquid line 30 by pulling one end of the replenishing liquid line 30 out of the replenishing liquid bag 31 in the same manner as the blood purification device 1 of FIG. 1. In addition, in the blood purification device 1b, the pre-replacement pump 39 is used as the liquid feed pump 6 for sending the purified plasma and air during the liquid recovery process. The air introduced by the air introduction unit 9 is sent to the chamber 27 through the replenishing liquid line 30, the pre-replacement pump 39, the plasma purifier 11 and the purified plasma feed line 38, and the purified plasma and the replenishing liquid are recovered.

In addition, in the blood purification device 1b, the liquid level height in the chamber is maintained at a predetermined liquid level height by the liquid level adjustment unit 8 during the liquid recovery process in the same manner as the blood purification device 1 described above. In particular, the control unit 7 starts discharge of air from the inside of the chamber 27 by driving the level adjustment pump 81 when a gas is detected by the first and second liquid level detection sensors 91, 92, and stops the discharge of air by stopping the level adjustment pump 81 when a gas is not detected by the first and second liquid level detection sensors 91, 92. The control unit 7 also calculates the accumulated value of the rotation amount of the level adjustment pump 81 and ends the liquid recovery process by stopping the level adjustment pump 81 and the liquid feed pump 6 (the pre-replacement pump 39 here) when the accumulated value of the rotation amount becomes not less than the predetermined threshold.

Summary of the Embodiments

Technical ideas understood from the embodiments will be described below citing the reference numerals, etc., used for the embodiments. However, each reference numeral, etc., described below is not intended to limit the constituent elements in the claims to the members, etc., specifically described in the embodiments.

[1] A blood purification device (1), comprising: a chamber (27) that is provided on a blood circuit (2) for extracorporeally circulating patient's blood and introduces purified plasma obtained by purifying plasma separated by a plasma separator (26) provided on the blood circuit (2), or a replenishing liquid for replenishing the plasma separated by the plasma separator, into the blood circuit (2); a liquid feed line (3) capable of sending the purified plasma or the replenishing liquid to the chamber (27); an air introduction unit (9) capable of introducing air into the liquid feed line (3); a liquid level adjustment unit (8) capable of adjusting a liquid level height in the chamber (27); and a control unit (7) that, at an end of blood purification treatment, performs a liquid recovery process for sending the purified plasma or the replenishing liquid to the chamber (27) via the liquid feed line (3) while introducing air into the liquid feed line (3) by the air introduction unit (9) and maintaining the liquid level height in the chamber (27) at a predetermined liquid level height by the liquid level adjustment unit (8).

The term "or" in [1] above means that at least one is applicable. For example, the expression "purified plasma or a replenishing liquid for replenishing the plasma separated by the plasma separator" means "at least one of purified plasma and a replenishing liquid for replenishing the plasma separated by the plasma separator (one of or both of them)".

[2] The blood purification device (1) described in [1], wherein the liquid level adjustment unit (8) is configured to be capable of increasing the liquid level height in the chamber (27) by discharging air from the inside of the chamber (27).

[3] The blood purification device (1) described in [2], comprising: a first liquid level detection sensor (91) being provided at a first height position of the chamber (27) and being capable of detecting whether or not a gas is present at the first height position in the chamber (27), wherein the control unit (7) causes the liquid level adjustment unit (8) to perform an operation of discharging air from the inside of the chamber (27) when a gas is detected by the first liquid level detection sensor (91).

[4] The blood purification device (1) described in [3], further comprising: a second liquid level detection sensor (92) being provided at a second height position of the chamber (27), which is higher than the first height position, and being capable of detecting whether or not a gas is present at the second height position in the chamber (27), wherein the control unit (7) starts discharge of air from the inside of the chamber (27) by the liquid level adjustment unit (8) when a gas is detected by the first and second liquid level detection sensors (91, 92), and stops the discharge of air by the liquid level adjustment unit (8) when a gas is not detected by the first and second liquid level detection sensors (91, 92).

[5] The blood purification device (1) described in any one of [1] to [4], comprising: a liquid feed pump (6) capable of sending the purified plasma or the replenishing liquid to the chamber (27), wherein, during the liquid recovery process, the control unit (7) drives the liquid feed pump (6) while introducing air into the liquid feed line (3) by the air introduction unit (9) and maintains the liquid level height in the chamber (27) at a predetermined liquid level height by the liquid level adjustment unit (8).

[6] The blood purification device (1) described in [5], wherein the liquid level adjustment unit (8) comprises a level adjustment pump (81) for discharging air from the inside of the chamber (27), and a discharge amount of the level adjustment pump (81) is not less than a discharge amount of the liquid feed pump (6).

[7] The blood purification device (1) described in [5] or [6], wherein the liquid level adjustment unit (8) comprises a level adjustment pump (81) for discharging air from the inside of the chamber (27), and the control unit (7) ends the liquid recovery process by stopping the level adjustment pump (81) and the liquid feed pump (6) when an accumulated value of a rotation amount of the level adjustment pump (81) becomes not less than a predetermined threshold.

[8] The blood purification device (1) described in any one of [5] to [7], wherein it is configured to discard the plasma separated by the plasma separator (26) and introduce the replenishing liquid into the blood circuit (2), the liquid feed line (3) comprises a replenishing liquid line (30) for sending a replenishing liquid, and the liquid feed pump (6) comprises a pump (35) provided on the replenishing liquid line (30) to send the replenishing liquid.

[9] The blood purification device (1a) described in any one of [5] to [7], comprising: a plasma purifier (10) for purifying plasma by adsorbing a specific component from the plasma separated by the plasma separator (26), wherein the liquid feed line (3) comprises a purified plasma feed line (38) for sending the purified plasma purified by the plasma purifier (10) to the chamber (27), and the liquid feed pump (6) comprises a waste liquid pump (44) provided on a waste liquid line (4) for sending the plasma separated by the plasma separator (26) to the plasma purifier (10).

[10] The blood purification device (1b) described in any one of [5] to [7], comprising: a plasma purifier (11) for purifying plasma by separating a specific component from the plasma separated by the plasma separator (26), wherein the liquid feed line (3) comprises a purified plasma feed line (38) for sending a mixture of the purified plasma purified by the plasma purifier (11) and the replenishing liquid to the chamber (27), and the liquid feed pump (6) comprises a pump (39) for sending the replenishing liquid to the plasma purifier (11).

[11] The blood purification device (1) described in any one of [1] to [5], wherein the liquid level adjustment unit (8) comprises an atmosphere release valve allowing the interior of the chamber (27) to be opened to atmosphere, and the control unit (7) increases the liquid level height in the chamber (27) by opening the atmosphere release valve and blocking the blood circuit (2) on a downstream side of the chamber (27).

Although the embodiments of the invention have been described, the invention according to claims is not to be limited the embodiments described above. In addition, all combinations of the features described in the embodiments are not necessary to solve the problem of the invention.

In addition, the invention can be appropriately modified and implemented without departing from the gist thereof. For example, the replenishing liquid is sent to the chamber 27 using the liquid feed pump 6 in the embodiments described above, but may be manually sent without using the liquid feed pump 6. For example, using an injector such as a cylinder connected to the air introduction unit 9, the liquid may be sent by injection pressure generated by manually operating the cylinder. Alternatively, the liquid feed pump 6 and the manual injector may be used in combination to send the liquid.

REFERENCE SIGNS LIST

1: blood purification device
2: blood circuit
24: blood pump
26: plasma separator
27: chamber
3: liquid feed line
30: replenishing liquid line
33: replenishing liquid transfer pump
35: total replacement pump
38: purified plasma feed line
39: pre-replacement pump
4: waste liquid line
44: waste liquid pump
6: liquid feed pump
7: control unit
8: liquid level adjustment unit
81: level adjustment pump
9: air introduction unit
10: plasma purifier
11: plasma purifier
91: first liquid level detection sensor
92: second liquid level detection sensor

The invention claimed is:
1. A blood purification device, comprising:
a blood circuit;
a plasma separator provided on the blood circuit, or a replenishing liquid for replenishing the plasma separated by the plasma separator, into the blood circuit;
a chamber that is provided on the blood circuit for extracorporeally circulating patient's blood and is configured to introduce purified plasma from the plasma separator provided on the blood circuit, or the replenishing liquid for replenishing the plasma separated by the plasma separator, into the blood circuit;
a liquid feed line configured to send the purified plasma or the replenishing liquid to the chamber;
an air introduction unit configured to introduce air into the liquid feed line;
a liquid level adjustment unit configured to adjust a liquid level height in the chamber so that the liquid level height is increased in the chamber by discharging air from an inside of the chamber;
a first liquid level detection sensor being provided at a first height position of the chamber and being configured to detect whether or not a gas is present at the first height position in the chamber;
a second liquid level detection sensor being provided at a second height position of the chamber, which is higher than the first height position, and being configured to detect whether or not the gas is present at the second height position in the chamber; and
a control unit that, at an end of blood purification treatment, is configured to:
perform a liquid recovery process to send the purified plasma or the replenishing liquid to the chamber via the liquid feed line,
introduce air into the liquid feed line by the air introduction unit while the liquid recovery process sends the purified plasma or the replenishing liquid to the chamber, and
maintain the liquid level height in the chamber at a predetermined liquid level height by the liquid level adjustment unit;
cause the liquid level adjustment unit to perform an operation of discharging air from the inside of the chamber when the gas is detected by the first liquid level detection sensor; and
start discharge of air from the inside of the chamber by the liquid level adjustment unit when the gas is detected by the first and second liquid level detection sensors, and
stop the discharge of air by the liquid level adjustment unit when the gas is not detected by the first and second liquid level detection sensors.

2. The blood purification device according to claim 1, comprising:
   a liquid feed pump configured to send the purified plasma or the replenishing liquid to the chamber via the liquid feed line,
   wherein, during the liquid recovery process, the control unit is configured to:
   drive the liquid feed pump,
   introduce air into the liquid feed line by the air introduction unit, and
   maintain the liquid level height in the chamber at a predetermined liquid level height by the liquid level adjustment unit.

3. The blood purification device according to claim 2, wherein the liquid level adjustment unit comprises a level adjustment pump configured to discharge air from the inside of the chamber, and
   wherein the level adjustment pump is configured to discharge an amount and the liquid feed pump is configured to discharge an amount that is not less than the amount of the level adjustment pump.

4. The blood purification device according to claim 2, wherein the liquid level adjustment unit comprises;
   a level adjustment pump configured to discharge air from the inside of the chamber, and
   wherein the control unit is configured to stop the level adjustment pump and the liquid feed pump when an accumulated value of a rotation amount of the level adjustment pump becomes not less than a predetermined threshold so that the liquid recovery process ends.

5. The blood purification device according to claim 2, wherein the blood purification device is configured to discard the plasma separated by the plasma separator and introduce the replenishing liquid into the blood circuit, the liquid feed line comprises a replenishing liquid line for sending the replenishing liquid, and the liquid feed pump comprises a pump provided on the replenishing liquid line to send the replenishing liquid.

6. The blood purification device according to claim 2, comprising:
   a plasma purifier for purifying plasma by adsorbing a specific component from the plasma separated by the plasma separator,
   wherein the liquid feed line comprises a purified plasma feed line for sending the purified plasma purified by the plasma purifier to the chamber, and the liquid feed pump comprises a waste liquid pump provided on a waste liquid line for sending the plasma separated by the plasma separator to the plasma purifier.

7. The blood purification device according to claim 2, comprising:
   a plasma purifier for purifying plasma by separating a specific component from the plasma separated by the plasma separator,
   wherein the liquid feed line comprises a purified plasma feed line for sending a mixture of the purified plasma purified by the plasma purifier and the replenishing liquid to the chamber, and the liquid feed pump comprises a pump for sending the replenishing liquid to the plasma purifier.

8. The blood purification device according to claim 1, wherein the liquid level adjustment unit comprises an atmosphere release valve allowing an interior of the chamber to be opened to atmosphere, and
   wherein the control unit is configured to:
   open the atmosphere release valve and block the blood circuit on a downstream side of the chamber to increase the liquid level height in the chamber.

9. The blood purification device according to claim 1, wherein the liquid level adjustment unit suppresses air bubbles from flowing downstream of the chamber by adjusting the liquid level height in the chamber.

10. The blood purification device according to claim 1, wherein the chamber is arranged upstream of an air bubble detector in the blood circuit.

* * * * *